United States Patent [19]

Lester et al.

[11] Patent Number: 4,651,560
[45] Date of Patent: Mar. 24, 1987

[54] METHODS OF AN APPARATUS FOR MONITORING MECHANICAL EQUIPMENT'S OPERATIONAL CONDITION

[75] Inventors: Michael F. Lester, Hednesford; Alan Brooks, Heather, both of England

[73] Assignee: National Coal Board, London, England

[21] Appl. No.: 830,923

[22] Filed: Feb. 19, 1986

[30] Foreign Application Priority Data

Feb. 19, 1985 [GB] United Kingdom ................. 8504194

[51] Int. Cl.⁴ ............................................. G01N 33/30
[52] U.S. Cl. ........................................ 73/64; 73/118.1
[58] Field of Search ....................... 73/64, 118.1, 10, 7, 73/162

[56] References Cited

U.S. PATENT DOCUMENTS 4,047,814  9/1977  Westcott ............................ 73/64 X

FOREIGN PATENT DOCUMENTS 108731  7/1982  Japan .................................... 73/162

*Primary Examiner*—Jerry W. Myracle
*Attorney, Agent, or Firm*—James C. Wray

[57] ABSTRACT

Samples of lubrication fluid are taken at relatively long sampling periods. Upon the derived rate of change of the amount of an inspected constituent differing by more than an acceptable value the lubrication fluid is changed and two further samples are taken over a relatively short sampling period. The rate of change in the amount of inspected constituent and the relatively short sampling period gives an indication of the operational condition of the mechanical equipment.

9 Claims, 3 Drawing Figures

METHODS OF AN APPARATUS FOR MONITORING MECHANICAL EQUIPMENT'S OPERATIONAL CONDITION

This invention relates to methods of and apparatus for monitoring mechanical equipment's operational condition, the equipment containing lubrication fluid.

In particular, although not exclusively, the invention relates to monitoring the operational condition of a gearbox installed in an underground mine where, typically, the gearbox is required to operate continuously in a remote and hazardous environment.

In such an installation the gearbox is either left to operate until it fails requiring mine production to be halted until the gearbox is replaced, or, alternatively, the gearbox is replaced at a more convenient time after a preselected operational period which is sufficiently short to avoid gearbox breakdown. The first adopted alternative tends to result in lost mine production and the second adopted alternative tends to result in needless gearbox replacement, a replaced gearbox usually being in a good operational condition.

An object of the present invention is to provide a method of and apparatus for monitoring a gearbox's operational condition which tends to overcome or reduce the above mentioned problems.

Accordingly, one aspect of the present invention provides a method of monitoring a mechanical equipment's operational condition, the equipment containing lubrication fluid, comprising the steps of taking and inspecting samples of lubrication fluid at relatively long sample periods, determining the amount of an inspected constituent present in each sample and comparing each determined amount with a previously determined amount to derive the rate of change in the amount of inspected constituent, indicating when the derived rate differs from the preselected acceptable rate value by an unacceptable value, changing the lubrication fluid upon the derived rate differing from the preselected acceptable rate value by an unacceptable value, taking at least two samples of lubrication fluid over a relatively short sampling period, and further deriving the rate of change in the amount of inspected constituent over the relatively short sampling period and thereby determining the operational condition of the mechanical equipment.

Advantageously, the method further takes into account the amount of operational running done by the mechanical equipment in each sample period.

Advantageously, the mechanical equipment is replaced if the further derived rate of change in the amount of the inspected constituent is more than a preselected rate value.

Preferably, the inspected constituent comprises ferrous material debris generated as the mechanical equipment wears.

Alternatively, the inspected constituent comprises a contaminant tending to pollute the lubrication fluid.

A second aspect of the present invention provides apparatus for monitoring the operational condition of mechanical equipment containing lubrication fluid according to the above defined method, the apparatus comprising means for taking samples of lubrication fluid at relatively long sample periods, inspection means for inspecting the samples and for determining the amount of an inspected constituent present in each sample indicator, means for indicating when the derived rate of change in the amount of the inspected constituent present in a sample differ from a preselected rate value by an unacceptable value, the occurrence of such an indication requiring a change of the lubrication fluid contained in the mechanical equipment, and processor means for further deriving the rate of change in the amount of the inspected constituent in at least two samples taken over a relatively short sample period after the lubrication fluid has been changed.

Preferably, the indicator means is adapted to take account of the amount of operational running done by the mechanical equipment in each sample period.

Preferably, the inspection means is adapted to inspect each sample to determine the amount of ferrous material debris generated as the mechanical equipment wears.

Alternatively, the inspection means is adapted to inspect each sample to determine the amount of a contaminant tending to pollute the lubrication fluid.

By way of example, one embodiment of the present invention will be described with reference to the accompanying drawings in which.

Figure 1:
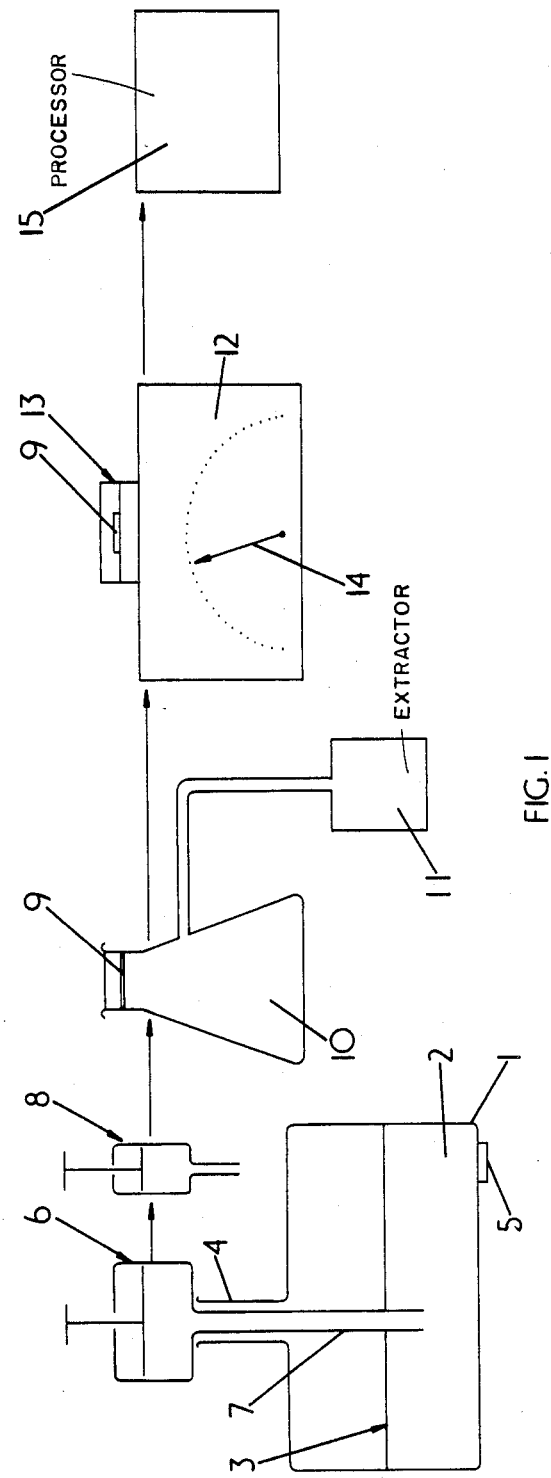
FIG. 1 shows a block diagram of apparatus according to thie invention.

In FIG. 1 a gearbox 1 is shown containing lubrication fluid 2 to a level 3. For the sake of clarity no gearing is shown in the gearbox. A normally closed inlet 4 to the gearbox is provided for adding lubrication fluid to the gearbox and a drain plug 5 is provided in the sump of the gearbox.

Syringe apparatus 6 is provided for taking relatively large samples of lubrication fluid from the gearbox. During normal operational running samples are taken from the gearbox at relatively long sample periods (for example every week). The syringe apparatus is provided with an elongate sampling tube 7 of such length that when the syringe apparatus is mounted on the gearbox inlet 4 the open end of tube 7 lies approximately mid way between the gearbox floor and the upper level of the lubrication fluid. The open end of the tube 7 is arranged away from the bottom of the gearbox to avoid extracting relatively heavy sludge which tends to collect in the bottom of the gearbox. Before taking a sample of lubrication fluid, the gearbox should be run for a sufficiently long period of time to ensure the fluid is to running temperature and mixed to a uniform consistency. The sampe is taken within five minutes of the machine ceasing operation.

Each relatively large sample of lubrication fluid (for example, 60 ccs) is placed in a container (not shown) for conveyance to an analysis laboratory. Once in the laboratory the container is heated to running temperature and shaken before a second syringe 8 takes a relatively small sample from the container, the volume of the relatively small sample being preselected (for example, 20 ccs) and carefully controlled. The 20 ccs is discharged into a mixing beaker where a solvent is added to assist ease of flow through the filter assembly. It then is poured on to a filter paper 9 located in vacuum filter apparatus 10 provided with an extractor device 11.

Upon the relatively small sample of lubrication fluid being filtered, the filter paper including the collected debris from the sample (for example ferrous material accruing from gearbox wear) is placed in a testing chamber 13 of debris testing equipment 12 arranged to derive a signal indicative of the total amount of the inspected constituent (for example, ferrous material debris) on the filter paper. Typically the determined amount of the inspected constituent is indicated on dial indicator means 14.

The indicated amount of the inspected constituent is fed to processor means 15 which monitors and compares the amount and indicates the rate of change in the amount of inspected constituent over the last sampling period. The processor means 13 further monitors and compares the amount of operational running done by the gearbox during the last sampling period and takes this into account in deriving the rate in the change of the inspected constituent. This further information is not derived by the debris test instrument but is derived from information fed into the computer using the appropriate software. The processor means is adapted to give the indicated values on a screen and/or a printer reader.

Upon the derived rate of change in the amount of inspected constituent differing from a preselected acceptable rate value by an unacceptable value this is taken as an indication that an operational problem may exist in the gearbox. The whole of the lubrication fluid in the gearbox is changed and the gearbox is run until the renewed fluid has reached an operational temperature. A further sample is taken and processed followed after a relatively short sample period by a further sample (for example the relatively short sample period may comprise an eight hour shift or twenty-four hours).

The processor means 15 compares the indicated values from the two samples taken over the relatively short sample period and derives the rate of change in the amount of inspected constituent. The derived rate is taken as an indication of the operational condition of the gearbox and if the derived rate differs from a preselect value by an unacceptable value the gearbox is withdrawn from service and replaced by a new gearbox.

The processor means 15 also monitors any additions of lubrication fluid and compensates the rate of change indication value to take account of the additional quantity of clean fluid.

In the case where the inspected constituent is ferrous material debris, the rate of increase in the amount of debris in the lubrication fluid is taken to indicate the amount of gearbox wear taking place. Any detected sudden increase in the amount of debris in the fluid indicates wear above that normally expected for the monitored operational running period.

Figure 2:
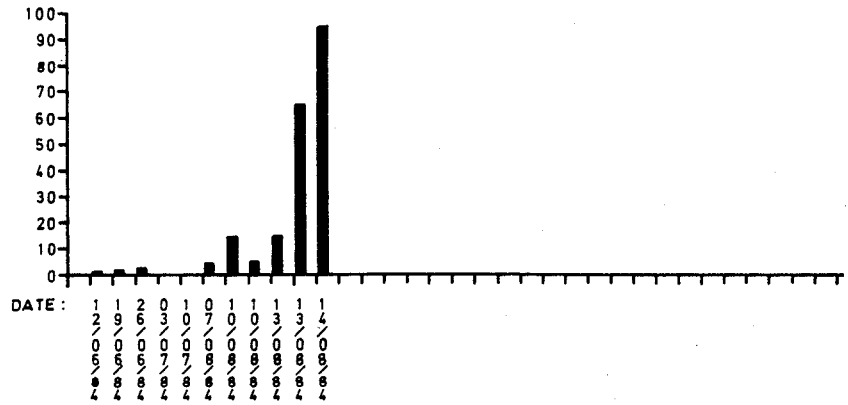
FIG. 2 shows a plot of derived values of the amount of an inspected constituent and details of work carried out during the monitoring.
Figure 3:
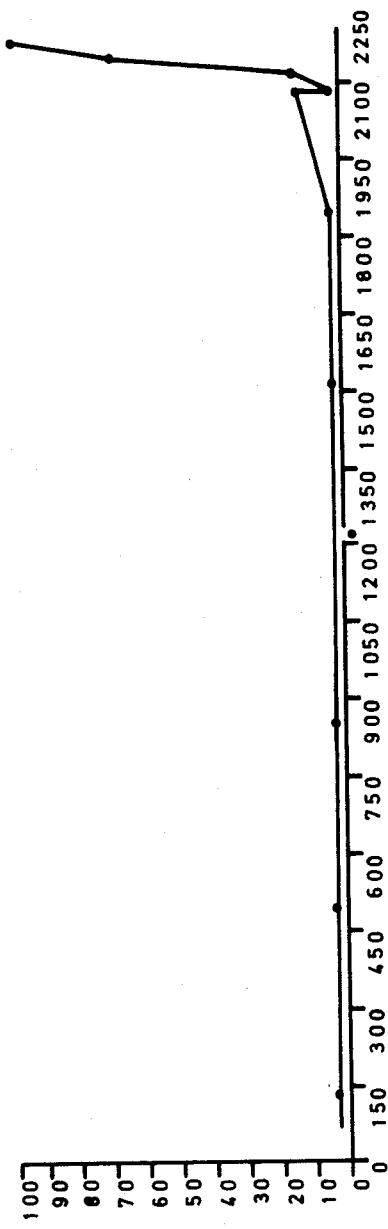
FIG. 3 shows a graph of derived values of the amount of the inspected constituent against an indication of operational running of the mechanical equipment.

FIGS. 2 and 3 show details monitored and derived during the monitoring of a conveyor gearbox in an underground mine.

FIG. 2 shows the plot of the amounts of ferrous material debris derived from eleven samples of lubrical oil taken from the gearbox. As can be seen from the figure the first six samples were taken over weekly sample periods. The rate of increase in the amount of debris derived in the seventh sample was more than an acceptable value. Consequently, on the Aug. 10, 1984 the gearbox oil was changed. The eighth sample was taken shortly after the oil was replaced and as would be expected indicate a relatively low amount of debris in the sample. However, the remaining three samples taken on relatively short sample periods show the increase in the rate of debris derived for the samples and on the Aug. 14, 1984 the gearbox was changed. Although gearbox appeared to be running satisfactorily before being changed a later detailed examination showed extending wear and damage.

FIG. 2 also shows indicated values derived by the processor means and fed to the printer reader. The light numbers on dark background indicate the unacceptable values.

FIG. 3 shows the derived values compensated for the amount of working face advance, the latter parameter is taken as proportional to the operational running period of the gearbox. Again the high values prior to the oil being changed and prior to the gearbox being changed are clearly indicated.

In other instances the inspected constituent comprises contaminant tending to pollute the lubrication fluid (for example dirt particles or foreign liquid tending to enter the gearbox).

We claim:

1. A method of monitoring a mechanical equipment operational condition, the equipment containing lubrication fluid, comprising the steps of taking and inspecting samples of lubrication fluid at relatively long sample periods, determining the amount of an inspected constituent present in each sample and comparing each determined amount with a previously determined amount to derive the rate of change in the amount of inspected constituent, indicating when the derived rate differs from the preselected acceptable rate value by an unacceptable value, changing the lubrication fluid upon the derived rate differing from the preselected acceptable rate value by an unacceptable value, taking at least two samples of lubrication fluid over a relatively short sampling period, and further deriving the rate of change in the amount of inspected constituent over the relatively short sampling period and thereby determining the operational condition of the mechanical equipment.

2. A method as claimed in claim 1, including the step of taking into account the amount of operational running done by the mechanical equipment in each sampling period.

3. A method as claimed in claim 2, wherein the mechanical equipment is replaced if the further derived rate of change in the amount of the inspected constituent is more than a preselected rate value.

4. A method as claimed in claim 3, wherein the inspected constituent comprises ferrous material debris generated as the mechanical equipment wears.

5. A method as claimed in claim 3, wherein the inspected constituent comprises a contaminant tending to pollute the lubrication fluid.

6. Apparatus for monitoring the operational condition of mechanical equipment containing lubrication fluid, the apparatus comprising means for taking samples of lubrication fluid at relatively long sample periods, inspection means for inspecting the samples and for determining the amount of an inspected constituent present in each sample, indicator means for indicating when the derived rate of change in the amount of the inspected constituent present in a sample differ from a preselected rate value by an unacceptable value, the occurrence of such an indication requiring a change of the lubrication fluid contained in the mechanical equipment and processor means for further deriving the rate of change in the amount of the inspected constituent in at least two samples taken over a relatively short sample period after the lubrication fluid has been changed.

7. Apparatus as claimed in claim 6, in which the indicator means is adapted to take account of the amount of operational running done by the mechanical equipment in each sample period.

8. Apparatus as claimed in claim 7, in which the inspection means is adapted to inspect each sample to determine the amount of ferrous material debris generated as the mechanical equipment wears.

9. Apparatus as claimed in claim 7, in which the inspection means is adapted to inspect each sample to determine the amount of a contaminant tending to pollute the lubrication fluid.

* * * * *